(12) United States Patent
Steube (10) Patent No.: US 8,540,686 B2
(45) Date of Patent: Sep. 24, 2013

(54) BLUNT TIP VIAL ACCESS CANNULA

(75) Inventor: Gregory A. Steube, St. Charles, MO (US)

(73) Assignee: Covidien AG (CH)

( * ) Notice: Subject to any disclaimer, the term of this patent is extended or adjusted under 35 U.S.C. 154(b) by 2001 days.

(21) Appl. No.: 11/070,314

(22) Filed: Mar. 2, 2005

(65) Prior Publication Data
US 2006/0200095 A1 Sep. 7, 2006

(51) Int. Cl.
*A61M 5/32* (2006.01)

(52) U.S. Cl.
USPC .......................... 604/272; 604/411

(58) Field of Classification Search
USPC ............... 604/272–274, 181, 187, 411–414
See application file for complete search history.

(56) References Cited

U.S. PATENT DOCUMENTS

| | | | | |
|---|---|---|---|---|
| 2,512,568 A | 6/1950 | Saffir | | 128/215 |
| 2,541,272 A | 2/1951 | Murphy | | |
| 2,590,895 A | 4/1952 | Scarpellino | | 128/221 |
| 2,746,455 A | 5/1956 | Abel | | |
| 2,752,919 A | 7/1956 | Gabriel | | |
| 2,954,768 A * | 10/1960 | Hamilton | | 604/274 |
| 2,989,053 A * | 6/1961 | Hamilton | | 604/411 |
| 3,076,457 A | 2/1963 | Copen | | 128/221 |
| 3,119,391 A | 1/1964 | Harrison | | 128/221 |
| 3,662,754 A | 5/1972 | Halloran | | 128/221 |
| 3,776,239 A | 12/1973 | Cooley | | 128/347 |
| 3,831,814 A | 8/1974 | Butler | | |
| 4,058,121 A * | 11/1977 | Choksi et al. | | 604/411 |
| 4,387,879 A | 6/1983 | Tauschinski | | |
| 4,505,709 A | 3/1985 | Froning et al. | | 604/411 |
| 4,675,020 A | 6/1987 | McPhee | | |
| 4,710,180 A | 12/1987 | Johnson | | |
| 4,723,955 A | 2/1988 | Vaillancourt | | |
| 4,743,243 A | 5/1988 | Vaillancourt | | 604/405 |
| 4,834,152 A | 5/1989 | Howson et al. | | 141/286 |
| 4,838,877 A | 6/1989 | Massau | | |
| 4,842,591 A | 6/1989 | Luther | | |
| 4,990,140 A | 2/1991 | Black | | 604/192 |
| 5,059,172 A | 10/1991 | Sutherland et al. | | |
| 5,071,413 A | 12/1991 | Utterberg | | 604/283 |

(Continued)

FOREIGN PATENT DOCUMENTS

FR 2 845 276 4/2002

OTHER PUBLICATIONS

Sherwood Medical Industries Inc., Monoject Product Data Filter Aspiration Needle, Aug. 1973, pp. 1-8.

(Continued)

*Primary Examiner* — Kevin C Sirmons
*Assistant Examiner* — Phillip Gray
(74) *Attorney, Agent, or Firm* — Lisa E. Winsor, Esq.

(57) ABSTRACT

This present disclosure provides a non-coring vial access cannula which has sufficient structural strength that it may be made from a thermoplastic resin instead of metal, thus reducing the likelihood and severity of operator injury by an accidental needle stick. The vial access cannula of the present disclosure has (i) a needle hub suitable for receiving a hypodermic syringe or an IV set (e.g., a Luer lock), (ii) a cannula portion having a centrally disposed lumen, wherein the centrally disposed lumen terminates in one or more distal openings and is in fluid communication with the needle hub, and (iii) a solid tip member distal to the one or more distal openings, wherein the solid tip member has a blade with a cutting edge.

22 Claims, 9 Drawing Sheets

(56) References Cited

U.S. PATENT DOCUMENTS

| | | | |
|---|---|---|---|
| 5,167,642 A | 12/1992 | Fowles | |
| 5,188,620 A | 2/1993 | Jepson et al. | |
| 5,203,775 A | 4/1993 | Frank et al. | 604/256 |
| 5,211,638 A | 5/1993 | Dudar et al. | |
| 5,364,387 A | 11/1994 | Sweeney | 604/411 |
| 5,470,327 A | 11/1995 | Helgren et al. | |
| 5,584,819 A | 12/1996 | Kopfer | |
| 5,746,733 A | 5/1998 | Capaccio et al. | |
| 5,755,696 A | 5/1998 | Caizza | |
| RE35,841 E | 7/1998 | Frank et al. | 604/256 |
| 5,820,621 A | 10/1998 | Yale et al. | |
| 5,832,971 A | 11/1998 | Yale et al. | |
| 5,833,674 A | 11/1998 | Turnbull et al. | |
| 5,887,633 A | 3/1999 | Yale et al. | |
| 5,919,182 A | 7/1999 | Avallone | |
| 5,928,162 A | 7/1999 | Giurtino et al. | |
| 5,928,215 A | 7/1999 | Caizza et al. | |
| 5,976,115 A | 11/1999 | Parris et al. | |
| 6,206,858 B1 | 3/2001 | Kempen et al. | |
| 6,358,236 B1 | 3/2002 | DeFoggi et al. | |
| 6,394,979 B1 | 5/2002 | Sharp et al. | |
| 6,447,498 B1 | 9/2002 | Jepson et al. | |
| 6,585,697 B2 | 7/2003 | Kempen et al. | |
| 6,610,041 B2 | 8/2003 | Daubert et al. | |
| 6,616,632 B2 | 9/2003 | Sharp et al. | 604/117 |
| 6,635,043 B2 | 10/2003 | Daubert et al. | |
| 6,637,470 B2 | 10/2003 | Reihl et al. | |
| 6,715,520 B2 | 4/2004 | Andréasson et al. | |
| 6,832,994 B2 | 12/2004 | Niedospial, Jr. et al. | |
| 6,875,205 B2 | 4/2005 | Leinsing | |
| 6,921,395 B2 | 7/2005 | Carano et al. | |
| 2002/0019622 A1 | 2/2002 | Daubert et al. | |
| 2004/0024354 A1 | 2/2004 | Reynolds | |
| 2004/0039365 A1 | 2/2004 | Aramata et al. | |

OTHER PUBLICATIONS

Sherwood Medical Industries, Monoject Filter Aspiration Needle, An Efficient Stainless Steel Filter in a Needle Hub, 4 pages.
European Search Report (8 pages).

\* cited by examiner

BLUNT TIP VIAL ACCESS CANNULA

BACKGROUND

1. Technical Field

This present disclosure relates to a cannula useful for penetrating membranes or septums as commonly used in medication vials, intravenous bags, access ports and the like.

2. Description of the Related Art

Many standard containers for pharmaceuticals, medicaments and other substances are air and moisture-tight containers (e.g., vials) having elastomeric stoppers. The container contents are typically accessed by piercing the stopper with a cannulated needle apparatus such as a typical hypodermic needle and syringe. In many applications, the container contents are repeatedly accessed. For example, many injectable pharmaceuticals are packaged in multidose vials requiring a vial access for the withdrawal of each unit dose. Also, many pharmaceuticals are lypholysed in sterile vials for prolonged stability. Such packaging also requires multiple vial entries to reconstitute the contents and withdrawal of the reconstituted contents.

Typically, the elastomeric stoppers are pierced using a sharp metal cannulated needle; usually a needle suitable for intravenous injection. One problem that arises with this type of vial access is coring of the elastomeric stopper. Coring occurs as the vial access needle is urged through the stopper and the needle punches or cuts a small particle of rubber from the stopper. This stopper fragment either drops into the vial or becomes lodged in the cannula and possibly withdrawn into the syringe. In either case, the sterility of the container contents is compromised and, in the latter case, injection of particulate matter into the patient may occur.

The prior art discloses various vial access needles for aspiration of medication including vial access needles providing conically shaped forward tips and fluid dispensing side ports. See, for example, the MONOJECT® Filter Aspiration Needle (1973) manufactured by Sherwood Medical Industries Inc. and U.S. Pat. No. 4,058,121 to Choksi et al., which disclose vial access needles for aspiration of medication.

Therefore, it would be desirable to overcome the disadvantages and drawbacks of the prior art with a vial access cannula that employs structure that minimizes or eliminates coring of elastomeric stoppers. It would also be desirable if the vial access cannula is easily and efficiently manufactured.

SUMMARY

Accordingly, a cannula useful for penetrating membranes or septums as commonly used in medication vials, intravenous bags, access ports and the like is provided having a blunt tip vial access cannula that employs structure for penetrating vials and the like for prevent coring of elastomeric stoppers to prevent particulates from the stopper from invading the pharmaceutical or medicament to overcome the related disadvantages and drawbacks of the prior art. Desirably, the blunt tip vial access cannula includes a solid tip member structure that prevents coring of septums as commonly used in medication vials, intravenous bags, access ports and the like.

One particular embodiment of the present disclosure provides a non-coring cannula for use as a vial access needle. The cannula described herein has sufficient structural strength that it may be made from a thermoplastic resin instead of metal, thus reducing the likelihood and severity of operator injury by an accidental needle stick. The vial access cannula of the present disclosure includes (i) a needle hub suitable for receiving a hypodermic syringe or an IV set, (ii) a cannula portion having a centrally disposed lumen, wherein the centrally disposed lumen terminates in one or more distal openings and is in fluid communication with the needle hub, and (iii) a solid tip member distal to the one or more distal openings, wherein the solid tip member has a blade with a cutting edge. In preferred embodiments, the centrally disposed lumen terminates in two distal openings and the distal openings are oriented such that the fluid flow is transverse to the axis of the centrally disposed lumen.

Preferably, the blade is disposed at an angle $\alpha$ of about 5-45° from the vertical plane perpendicular to the longitudinal axis of the cannula, and most preferably, the blade is disposed at an angle of about 10-20°.

In another illustrative embodiment, the solid tip member of the vial access cannula has one or more bevels such that the vertical length of the cutting edge is about 50-95% of the diameter of the cannula portion. The bevels that cause the length reduction of the cutting blade are disposed medially at an angle of about 5-25°, and most preferably, about 8-15°.

In another embodiment, the vial access cannula has lateral facets spanning the distal end of the cannula portion, from a point proximal to the lateral openings, and the proximal end of the solid tip member. In preferred embodiments, the distal boundary of the lateral facet is the proximal edge of the bevel that forms the cutting edge of the blade. In another embodiment, there is an additional laterally disposed bevel between the distal boundary of the facet and the bevel that forms the cutting edge. In one embodiment, the laterally disposed facets contain a medial groove which is disposed parallel to the longitudinal axis of the vial access cannula. Typically, the medial grooves have substantially the same width as the distal openings of the centrally disposed cannula and run distally from the distal openings. On the distal end, the medial grooves terminate prior to the proximal boundary of the bevel that forms the cutting edge.

In particularly useful embodiments, the interior wall of the needle hub is tapered which facilitates a Luer slip-type of connection. In other embodiments, the needle hub contains a female portion of a Luer lock (i.e., the Luer wings). Optionally, the needle hub, the flange, or the proximal end of the centrally disposed cannula may contain a filter. Useful filters include membrane filters (e.g., PVDF or methylcellulose), or microporous metal (e.g., stainless steel) filters.

BRIEF DESCRIPTION OF THE DRAWINGS

The foregoing and other features and advantages of the present disclosure will be more fully understood from the following detailed description of the exemplary embodiments, taken in conjunction with the accompanying drawings in which.

DETAILED DESCRIPTION OF THE EXEMPLARY EMBODIMENTS

The exemplary embodiments of the blunt tip vial access needle disclosed herein are discussed in terms of cannulated needle devices for infusion of intravenous fluids, medication infusion and fluid collection, and more particularly, in terms of manually accessing vials of pharmaceuticals and the like housed in containers that employ septum structures that require access such as medication vials, intravenous bags, access ports and the like. It is contemplated that the cannula may be shielded during storage, transport, fluid infusion and/or collection and subsequent thereto.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the safety apparatus. According to the present disclosure, the term "clinician" refers to an individual administering an infusion, performing fluid collection, installing or removing a needle cannula from a safety apparatus and may include support personnel.

Additionally, the term "cutting edge" refers to the union of one or more bevels and is located at the distal end of the cannula. The term "slanted blade" refers to a cutting edge, together with one or more bevels that form the cutting edge, in which the angle of the cutting edge is less than perpendicular to the longitudinal axis of the cannula to which it is attached.

The following discussion includes a description of the blunt tip vial access cannula, in accordance with the present disclosure. Reference will now be made in detail to the exemplary embodiments of the disclosure, which are illustrated in the accompanying figures.

Figure 1:
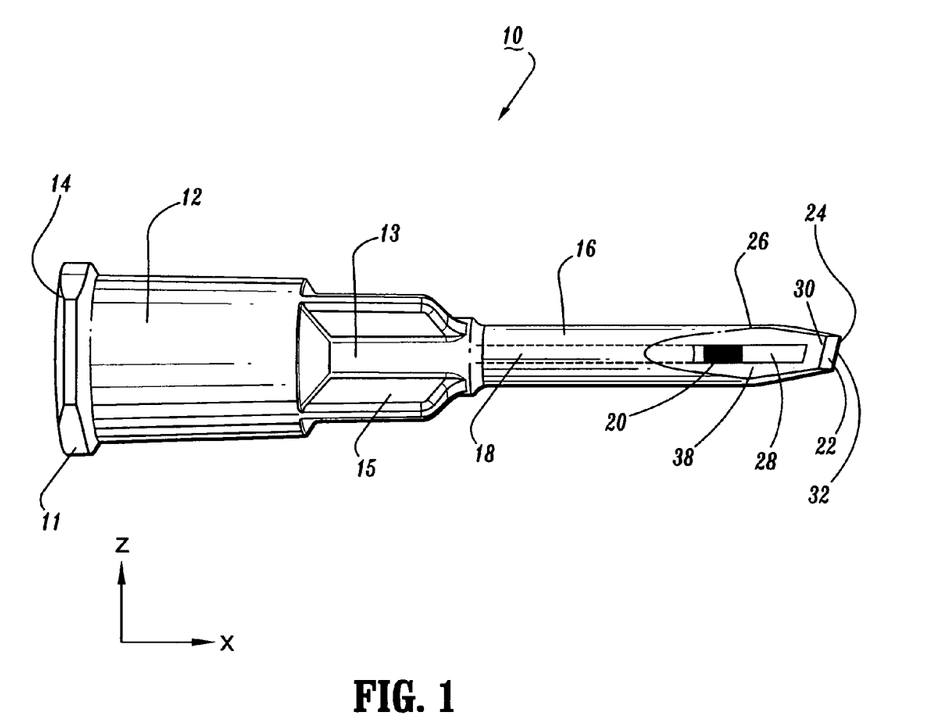
FIG. 1 is a perspective view of a cannula constructed in accordance with the principles of the present disclosure.
Figure 2:
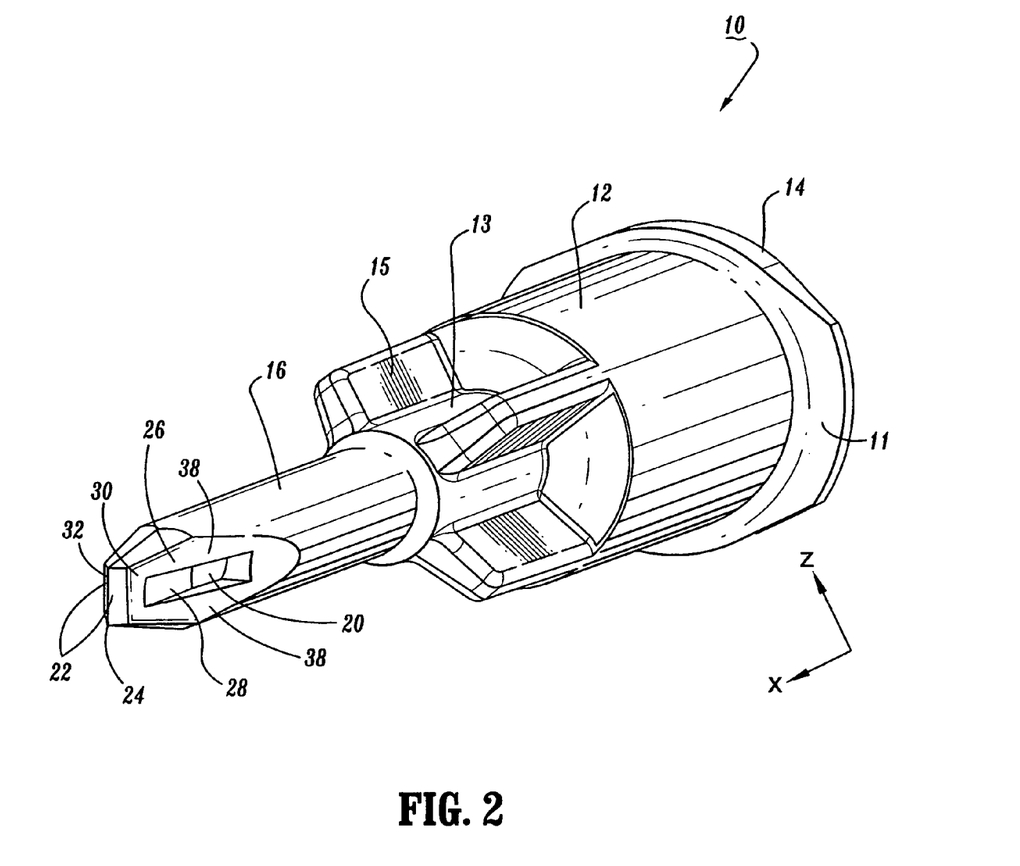
FIG. 2 is a perspective view of the cannula according to FIG. 1.

Turning now to the figures, wherein like components are designated by like reference numerals throughout the several views. Referring to FIGS. 1 and 2, the present disclosure provides a non-coring vial access cannula 10. Preferably, the cannula 10 is molded from plastic into a unitary structure; however, it is contemplated that the cannula of the present disclosure may be fabricated from metal alloys. The cannula 10 includes a needle hub 12 at a proximal end 14 thereof. The cannula 10 in this construction further includes a flange portion 13, which is intermediately disposed between needle hub portion 12 and a cannula portion 16. Cannula portion 16 includes a centrally disposed lumen 18 (shown in phantom), which terminates in two distal openings 20. It is contemplated within the present disclosure that cannula portion 16 may terminate in one or more distal openings 20. The cannula 10 terminates at its distal end 24 in a solid tip member 26. The solid tip member 26 is distal to the distal openings 20 of the centrally disposed lumen 18.

The needle hub 12 is designed to receive a syringe or an IV set (not shown) and, in preferred embodiments, comprises the female portion of a Luer Lock 11 (i.e., has "ears" for mating with the threaded male Luer connector). Preferably, the interior wall of the needle hub 12 is tapered distally for providing a frictional fit with received syringes or IV sets (i.e., capable of functioning as a Luer slip connection). Other configurations of the needle hub 12 are possible and depend upon each particular receiving syringe or device with which the cannula 10 of the present disclosure will be used.

The centrally disposed lumen 18 extends through the flange 13 and is in fluid communication with the needle hub 12 at the proximal end 14. The centrally disposed lumen 18 terminates in one or more distal openings 20. In preferred embodiments, distal openings 20 are laterally disposed to the central longitudinal X-axis of the cannula 10. In other preferred embodiments, the lumen 18 terminates with two opposing distal openings 20, which are oriented at 90° to the cutting edge of cutting edge 32.

Optionally, the needle hub 12 may include a filter within the centrally disposed lumen 18 or the interior portions of flange 13 or hub 12. Particularly useful filters include, for example, a microporous stainless steel filter. Suitable filters include, for example, 0.22 μm and 0.45 μm membrane filters, and 5 μm random path membrane filters. The choice of needle hub filter is left to the practitioner based on each specific application. Generally, the manufacture and use of needle hub filters is well known in the art.

During operation, the flange portion 13 is designed to engage a top portion of the vial or elastomeric stopper into which the cannula 10 is to be inserted such that the flange 13 limits the depth of cannula 10 penetration through the elastomeric stopper. There is no specific requirement for the shape of the flange 13, but in preferred embodiments, it contains one or more wing or stop members 15 symmetrically distributed around the flange 13 circumference and extending radially outwards. Preferably, neither the flange 13 nor its wings 15 extend outward beyond the width of the needle hub 12.

The solid tip member 26 contains a slanted blade 30 containing a cutting edge 32 which is formed at the junction of the bevels 22. It is contemplated within the present disclosure that cutting edge 32 is not perpendicular (i.e., slanted) in relation to longitudinal X-axis of cannula 10. The slanted blade 30, including the cutting edge 30 and the bevels 22, facilitate penetration of the elastomeric stoppers and other vial closure devices. The solid tip member 26 further contains medial grooves 28 extending substantially from the distal openings 20 running in a distal direction parallel to the centrally disposed lumen 18, but terminating prior to the proximal edge of the bevels 22. The medial grooves 28 facilitate flow when fluid is drawn into the syringe (not shown) through the cannula 10.

The presence of medial grooves 28 assist manufacture of the device in the mold by diverting the stream of ejected fluid within the angle, most preferably about 45°, from the tip.

Cannula 10 includes an additional facet 38 bridging the distal end of the cannula portion 16 and the solid tip member 26. The facets 38 are typically symmetrical on each of the lateral sides of the cannula 10 and are oriented parallel to the cutting edge 32. The purpose of the facet 38 is to facilitate penetration of the solid tip member 26 and the cannula portion 16 of the cannula 10 through an elastomeric vial stopper. Cannulae without the facets 38 generally require the use of more force and are more prone to tear the vial stopper.

Figure 3:
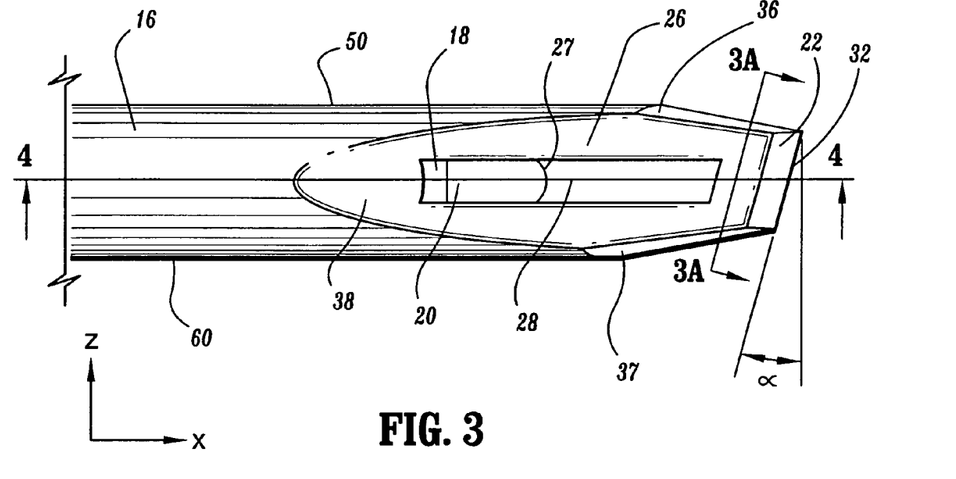
FIG. 3 is a plan view of a distal portion of the cannula according to FIG. 1.
Figure 3A:
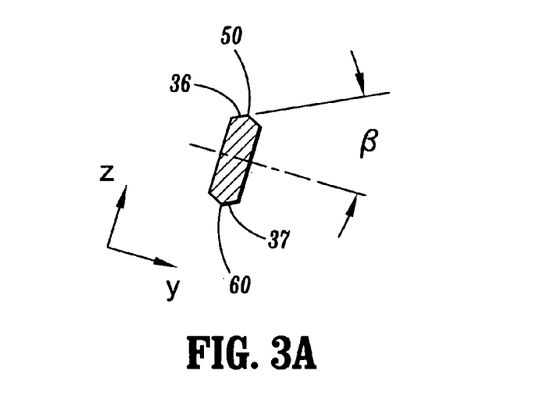
FIG. 3A is a cross-sectional view of the distal portion of the cannula, through plane 3A-3A, of FIG. 3.

With reference to FIGS. 3 and 3A, the distal end of the cannula portion 16 and a lateral view of solid tip member 26 are shown. More specifically, distal openings 20 are of equal widths, for example, about 0.025 mm, and are of substantially the same width as the diameter as the centrally-disposed lumen 18. The medial grooves 28 preferably have substantially the same width as the distal openings 20. The solid tip member 26 has one or more top bevels 36 along the first side 50 and one or more bottom bevels 37 along the second side 60. Although one pair of cutting bevels 22 and two pairs of side bevels 36 and 37 are shown, it is contemplated within the present disclosure that the solid tip member 26 include at least one cutting bevel and at least one side bevel.

Figure 6:
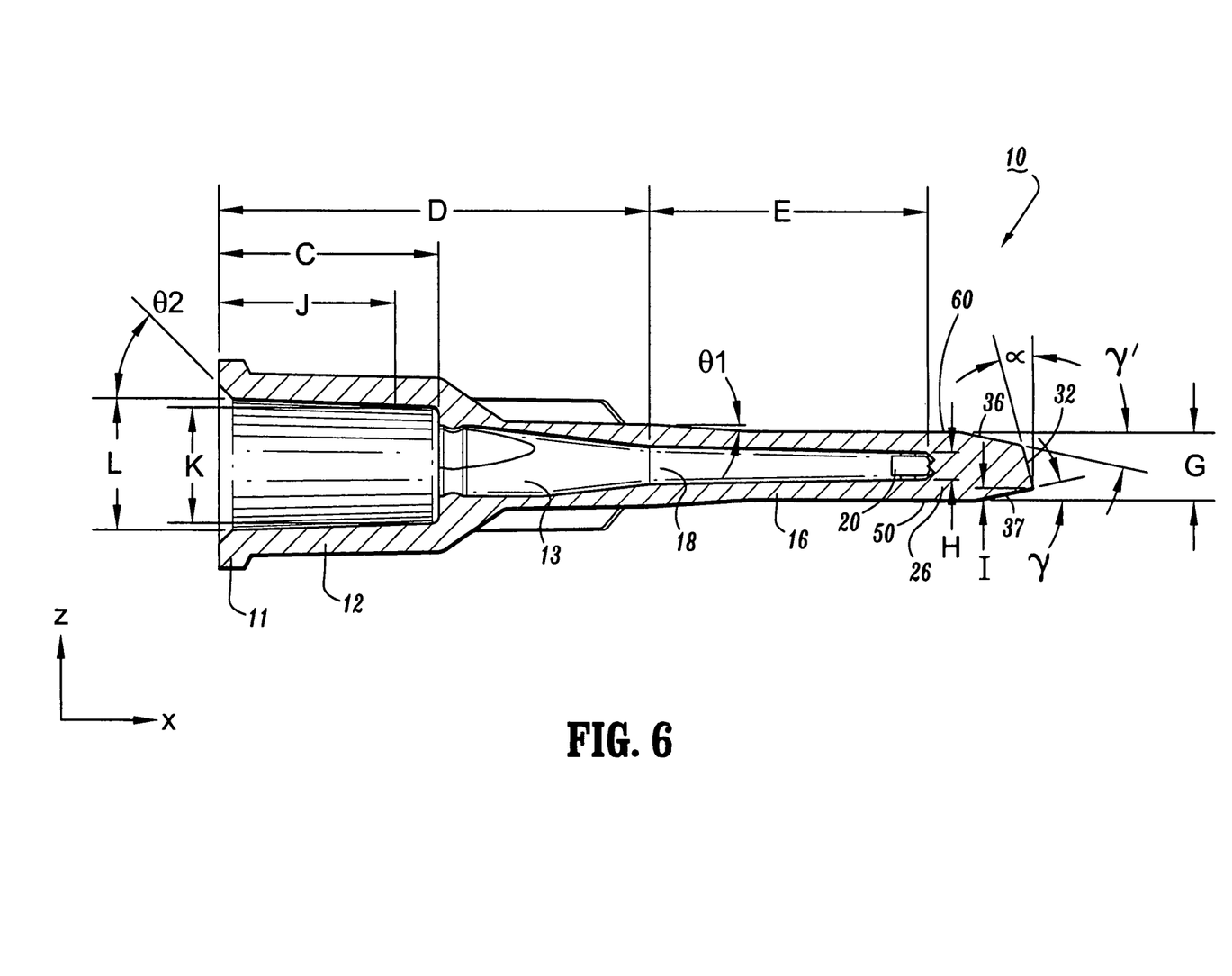
FIG. 6 is a cross-sectional plan view of the cannula, though plane 6-6, of FIG. 5.

The cutting edge 32 of the slanted blade 30 is disposed at an angle α of preferably about 5-45°, more preferably 10-30° and most preferably about 10-20°, to vertical axis (Z-Z) shown as perpendicular to the longitudinal X-axis of the cannula 10 (FIGS. 3 and 6). The bevels 36 and 37 effectively reduce the length of the cutting edge 32 and facilitate penetration of the elastomeric vial stoppers. Preferably, the bevels 36 and 37 reduce the length of the cutting edge 32 by about 5-50% relative to the outer diameter of the cannula portion 16 making the vertical length of the cutting edge about 50-95% of the diameter of the cannula portion 16. Bevels 36 and 37 may be formed as a smooth arc or by two, three, four or more bevels and still perform substantially the same function. FIG. 3A shows a cross-section, through plane 3A-3A, of the solid tip member 26 having bevels 36 on the first side 50 and bevels 37 on the second side 60. In this embodiment, each bevel 36 and 37 are bisected forming two bevels, each at a bevel angle β to the Y-axis. While it is preferred that each bevel in a pair of bevels have the same bevel angle β, those angles could be different from each other. In preferred embodiments for which the bevels 36 and 37 have two bevels, the bevel angle β is preferably about 15-30°, more preferably about 17-27° and most preferably about 22-24°. Although it is preferable, for a cannula 10 having bevels 36 and 37 symmetrical in cross-section (FIG. 3A), symmetry is not required. For example, the first side 50 bevels 36 may have a rounded profile, while the second side 60 bevels 37 have a beveled profile. As shown in more detail in FIG. 6, the bevels 36 and 37 are medially disposed at an angle γ and γ', respectively, of preferably about 5-25°, more preferably about 7-20° and most preferably about 8-15° from the X-axis. It is contemplated within the present disclosure that angles γ and γ' may be equal or of different values from the X-axis. The purpose of the bevels 36 and 37 are to reduce the length of the cutting edge 32, thereby reducing the force required to urge the cannula 10 through an elastomeric stopper. The reduction in the length of the cutting edge 32 is a function of the bevel angle γ, the length, along the longitudinal X-axis, of the solid tip member 26, and the precise point of origin of the bevels 36 and 37 at their proximal edge.

Figure 4:
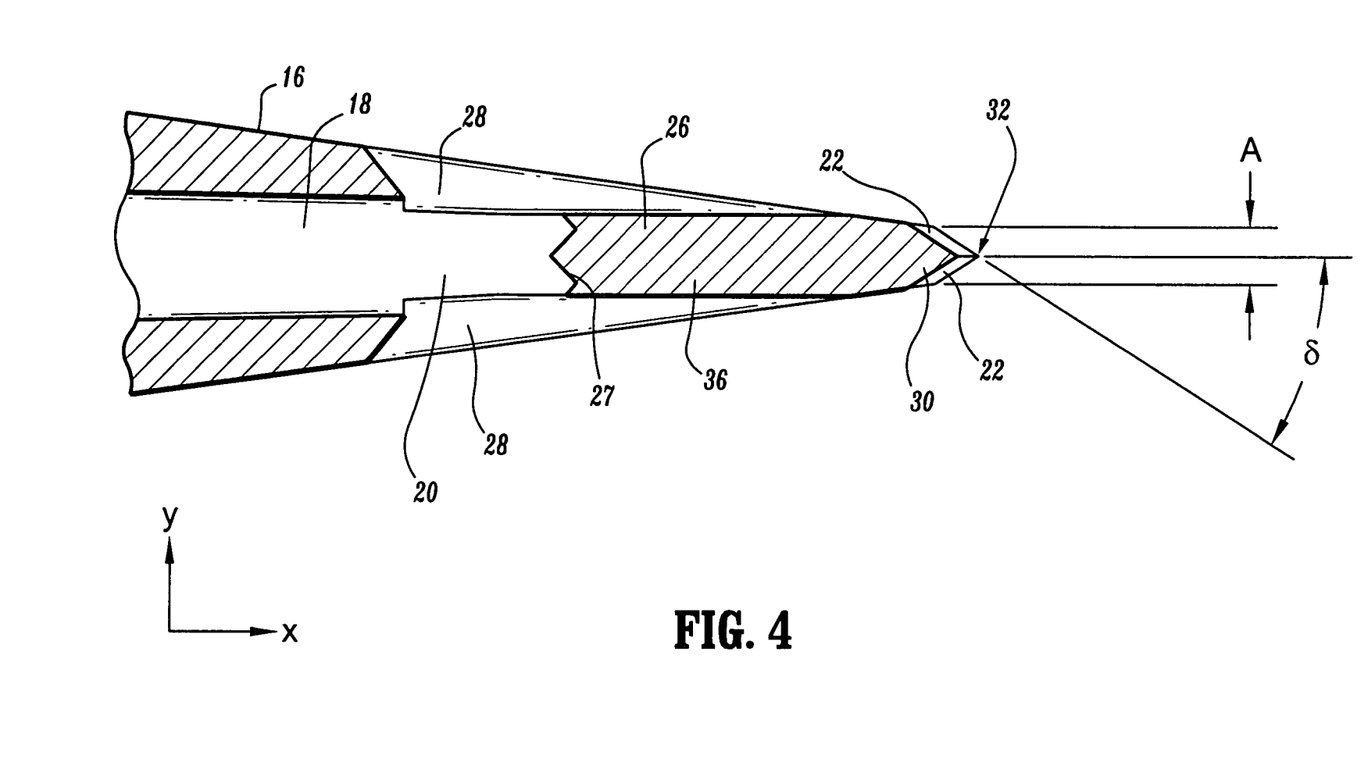
FIG. 4 is a cross-sectional side view of the cannula, through plane 4-4, of FIG. 3.

Turning now to FIG. 4, a preferred embodiment of the distal end of the cannula portion 16 and the solid tip member 26 in a cross-sectional top view through plane 4-4 of FIG. 3 is shown. The cutting edge 32 is formed at the union of the bevels 22. The bevels 22 each form an angle δ of preferably about 20-40°, more preferably about 25-35° and most preferably about 28-32° with the longitudinal X-axis of the cannula 10. In a preferred embodiment, the bevels 22 each form an angle of about 30° with the longitudinal X-axis of the cannula 10, resulting in the cutting edge 32 having a total inside angle of about 60°. The preferred width A of the slanted blade 30 is about 1.47 mm with each bevel 22 forming an angle δ of about 30° with the longitudinal X-axis.

Figure 4A:
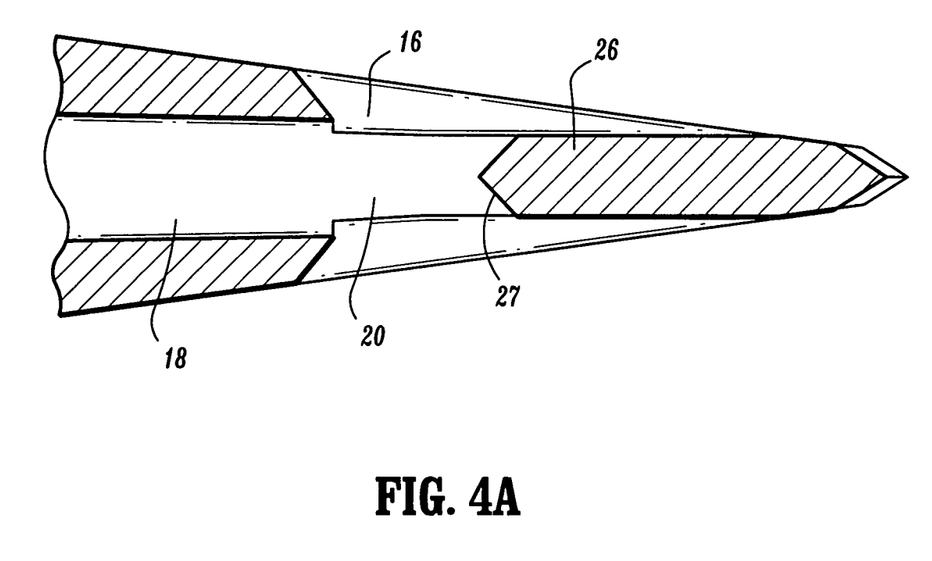
FIG. 4A is a partial callout cross-sectional side view of an alternative embodiment of the cannula, through plane 4-4, of FIG. 3.

With reference to FIG. 4A, there is disclosed a partial cross-sectional side view (through plane 4-4 of FIG. 3) of an alternative embodiment of the cannula portion 16. Centrally disposed lumen 18 of cannula portion 16 includes a distally situated terminating wall portion 27. Wall portion 27 may be formed in a variety of shapes including, for example, an arc shape (FIG. 3), plurality of frustoconical shapes (FIG. 4) or single frustoconical shape (FIG. 4A). The shape of wall portion 27 is formed by a terminal end of a core pin (not shown) used in the manufacture of cannula 10. During manufacture of cannula 10, a metal core pin having, for example, a single inverse frustoconical shape or inverse wedge shape, is used to form wall portion 27 as shown in FIG. 4A. The shape of wall portion 27 can be used to control or divert the flow of fluid through distal openings 20. For example, the delivery of fluid through distal openings 20 is best delivered (i.e., in a forward facing spray direction) less than ninety degrees (90°), and preferably less than forty-five (45°) from the longitudinal X-axis of the cannula 10.

Figure 5:
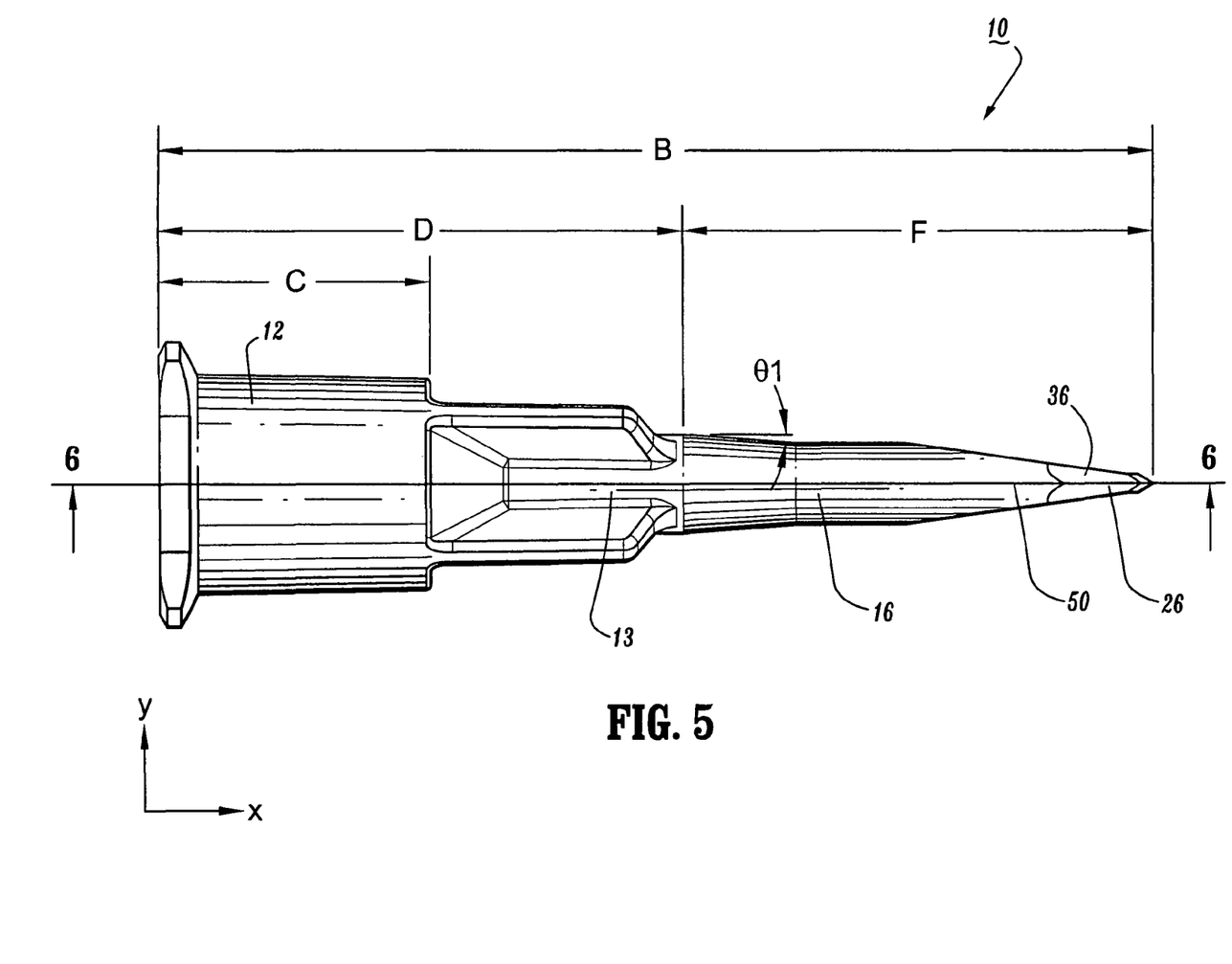
FIG. 5 is plan view of the cannula according to FIG. 1.
Figure 7:
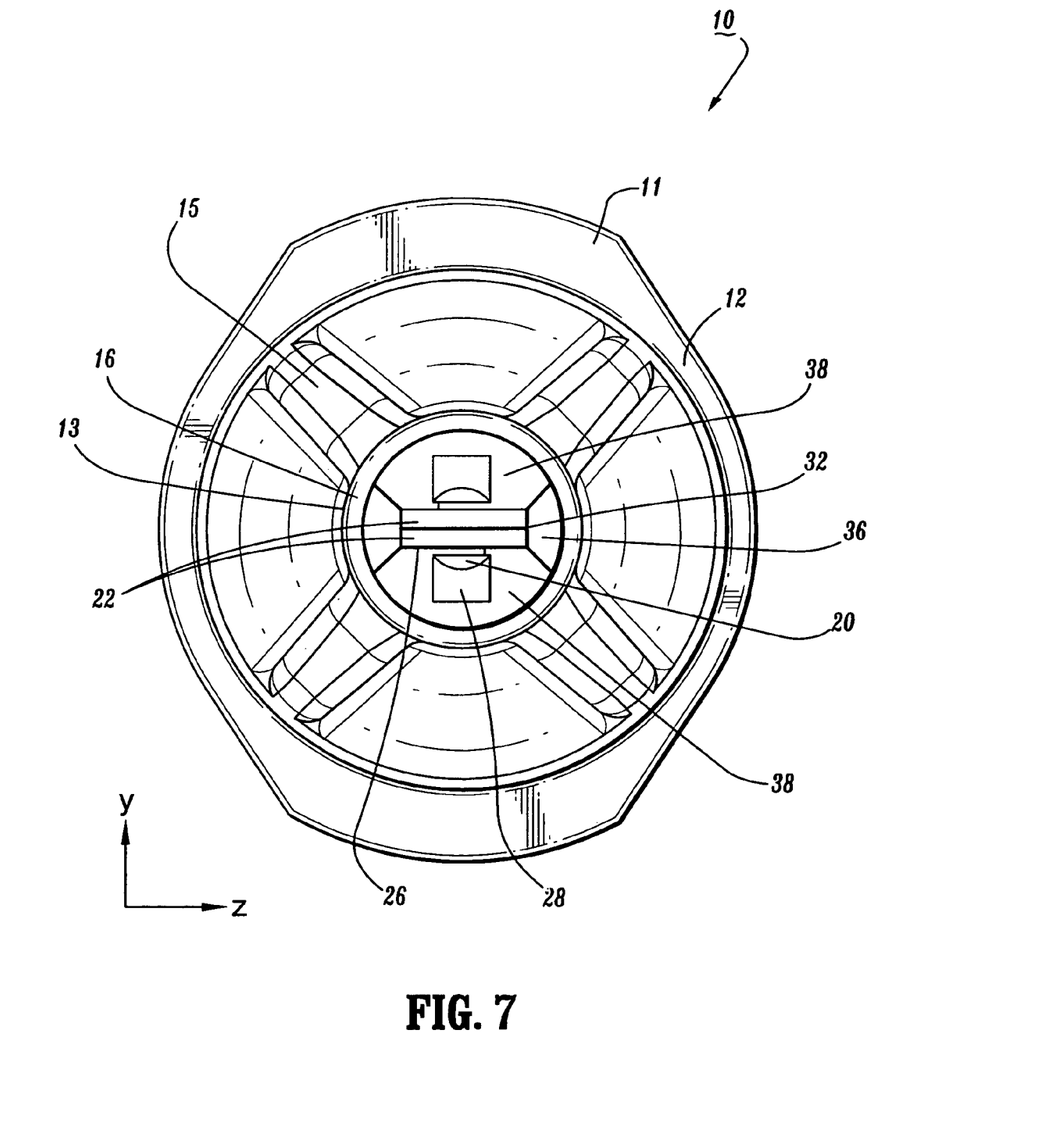
FIG. 7 is a top plan view of the cannula of the present disclosure according to FIG. 1.

With reference now to FIGS. 5-7, there is disclosed an alternate view of the cannula according to the present disclosure. These figures are described in terms of a preferred embodiment which is useful for many medical applications. Of course, the exact dimensions may be altered, within the scope of the disclosure, depending upon each particular application for which a vial access cannula 10 is required. FIG. 5 shows the preferred embodiment of the entire cannula 10 in top view. The overall length B of the cannula 10 is about 1.128 cm. The length C of the needle hub 12 is about 0.308 cm which, together with the flange portion 13, is about 0.595 cm in length D. The length E (FIG. 6) of the cannula portion 16 is about 0.386 cm (from the distal end of the flange portion 13 to the distal end of lumen 18), which together with the solid tip member 26 comprise a length F of about 0.533 cm. To facilitate penetration of the cannula 10 through an elastomeric stopper, optionally, the proximal region of the cannula portion 16 is tapered by forming an angle $\theta 1$ with the X-axis. Preferably, the angle $\theta 1$ is about 2-6° and more preferably about 4°. Tapering the proximal region of the cannula portion 16 preferably reduces the exterior diameter from about 0.106 cm at the junction with the flange portion 13 to about 0.088 cm at the distal end G. The centrally disposed lumen 18 may be tapered, either continuously or discontinuously, over the length of the cannula portion 16. Preferably, the centrally disposed lumen 18 has a diameter H of about 0.033 cm at the distal openings 20 and about 0.050 cm at its junction with the flange portion 13. The centrally disposed lumen 18 is preferably tapered in the flange portion 13.

As discussed above, in preferred embodiments, the solid tip member 26 has at least one bevel 36 on the first side 50 and at least one bevel 37 on the second side 60. Most preferably, each angle γ and γ' of the bevel is about 8-15°. In this preferred embodiment, which has both bevels 36 and 37 at about an 11° angle γ and γ', the vertical length of the cutting edge 32 is about 0.058 cm which represents a reduction of about 0.030 cm compared to the diameter G of the cannula portion 16. The 0.030 cm reduction in vertical length I is comprised of about a 0.015 cm reduction on both the first side 50 and the second side 60.

As discussed above, preferably, the needle hub 12 is mating with the male portion of a threaded Luer connector and/or functioning as a Luer slip connector. Suitable dimensions for these types of connectors are well known in the art. For example, the depth C of the syringe receiving portion of the needle hub 12 is about 0.305 cm and is flared over about the proximal 0.25 cm of depth J. In a suitable flared configuration, the needle hub 12 has a luminal diameter K of about 0.155 cm toward the distal end and a luminal diameter L of about 0.210 cm toward the proximal opening. The exterior diameter of the needle hub, excluding the Luer ears 11, is about 0.234 cm. In another preferred embodiment, the inner corner of the proximal opening of the needle hub 12 is beveled to an angle $\theta 2$, which facilitates entry of the syringe end into the needle hub 12. Suitably, $\theta 2$ may be about 30-55°, but preferably is about 45°.

With reference to FIG. 7, a bottom plan view of one embodiment of the cannula 10 is shown. In this embodiment, the needle hub 12 contains a Luer lock 11 which is oriented parallel to the cutting edge 32 (Z-axis). The flange portion 13 contains four flange wings 15, which are offset by 45° relative to the plane of the cutting edge 32 (the Z-axis). The flange wings 15 may, of course, be rotated to any convenient angle or may adopt different configurations if a number of flange wings 15 other than four are used. The cannula portion 16 terminates in two laterally disposed distal openings 20. The solid tip member 26 has two bevels 36, two medial grooves 28 and symmetrical lateral facets 38.

Figure 8:
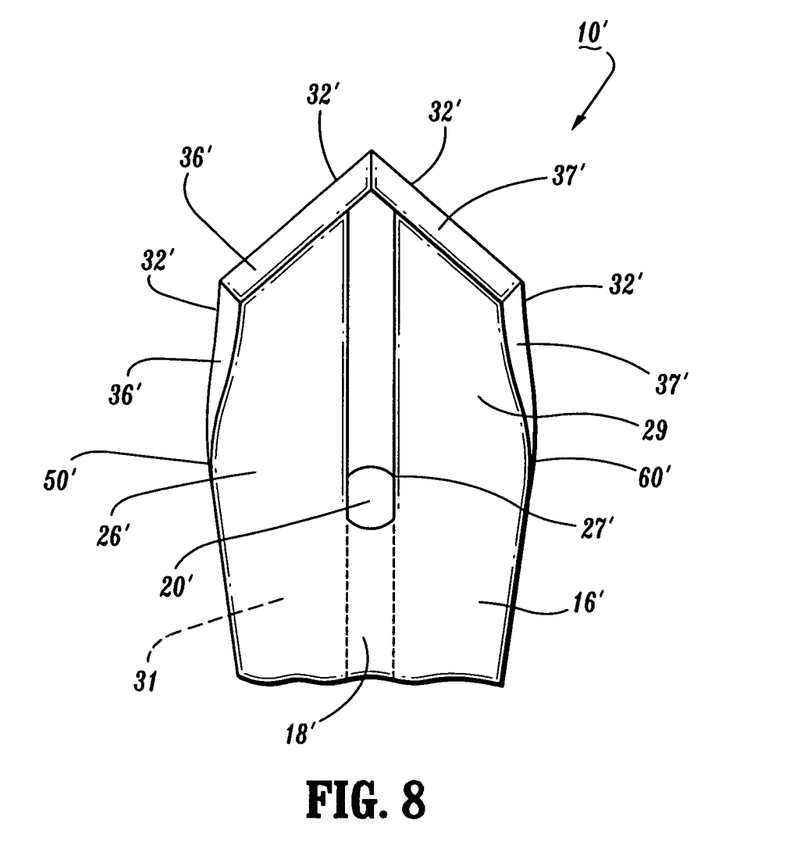
FIG. 8 is a partial plan view of an alternative embodiment of the cannula according to the present disclosure

With reference to FIG. 8, an alternative embodiment of cannula 10' includes a cannula portion 16' and solid tip member 26' having a first side 29. Cannula 10' includes lumen 18' (shown in phantom) terminating at wall portion 27' of distal opening 20'. The solid tip member 26' includes at least one cutting bevel and at least one side bevel. More specifically, solid tip member 26' includes one or more top bevels 36' along the first side 50' and one or more bottom bevels 37' along the second side 60'. The bevels 36' and 37' can be of certain lengths to effectively reduce the length of the cutting edges 32', which facilitates penetration of the elastomeric vial stoppers. Although multiple cutting edges 32' are shown, it is contemplated that one or more cutting edges 32' may be incorporated with solid tip member 26'. Bevels 36' and 37' may be formed as smooth arcs having flat or curved planes or flat or curved cutting edges, or by two or more bevels. Cannula portion 16' may include an opposite second side 31 formed as a mirror image of first side 29. Alternatively, opposite second side 31 may be formed as a flat surface having a plane substantially parallel to the longitudinal X-axis of cannula 10'.

Although the foregoing present disclosure has been described in some detail by way of illustration and example for purposes of clarity of understanding, it will be readily apparent to those of ordinary skill in the art in light of the teachings of this present disclosure that certain changes and modifications may be made thereto without departing from the spirit or scope of the appended claims.

What is claimed is:

1. A vial access cannula comprising:
   a needle hub;
   a cannula portion connected to the needle hub and having a centrally disposed lumen,
   wherein said centrally disposed lumen terminates in at least one distal opening and is in fluid communication with said needle hub;
   a solid tip member disposed distal to said at least one distal opening, wherein said solid tip member includes at least one blade having at least one beveled face that extends to a cutting edge, and wherein a blunt distal-most tip of the solid tip member is defined by the union of a plurality of edges, at least one of the plurality of edges disposed at an angle of less than about 45° from a vertical plane perpendicular to a longitudinal axis of the cannula; and
   at least one planar lateral facet defining an outwardly facing exterior surface of the vial access cannula, the at least one planar lateral facet spanning an exterior distal region of said cannula portion and an exterior proximal region of said solid tip member, and the at least one lateral facet includes a medial groove running distally from said at least one distal opening and terminates proximal to said at least one blade.

2. The vial access cannula of claim 1, wherein the at least one blade includes opposing beveled faces that extend to the cutting edge.

3. The vial access cannula of claim 1, wherein the solid tip member includes at least two beveled faces that extend to at least two cutting edges.

4. The vial access cannula of claim 1, wherein the centrally disposed lumen terminates in two distal openings and fluid flow through said distal openings is transverse to the axis of the cannula.

5. The vial access cannula of claim 1, wherein the at least one planar lateral facet comprises a pair of planar lateral facets, wherein said pair of planar lateral facets comprises a medial groove, and wherein said medial groove
   (i) is disposed parallel to the longitudinal axis of said cannula,
   (ii) has substantially the same width as said distal openings, and
   (iii) runs distally from said distal openings and terminates proximal to said at least one blade.

6. The vial access cannula of claim 1, wherein said at least one blade is disposed at an angle of about 5-45° from the vertical plane perpendicular to the longitudinal axis of the cannula.

7. The vial access cannula of claim 1, wherein said cutting edge of the at least one beveled face has a vertical length of about 50-95% of the diameter of the cannula portion.

8. The vial access cannula of claim 7, wherein each of said at least one beveled face is medially disposed at an angle of about 5-25° from a longitudinal axis of the cannula.

9. The vial access cannula of claim 1, wherein said needle hub comprises the female portion of a Luer lock.

10. The vial access cannula of claim 1, wherein said needle hub further comprises a filter.

11. The vial access cannula of claim 1, wherein said vial access cannula is molded from plastic.

12. A vial access cannula comprising:
    a needle hub, wherein said needle hub includes the female portion of a Luer lock;
    a cannula portion connected to the needle hub and having a centrally disposed lumen, wherein said centrally disposed lumen terminates in two laterally disposed distal openings and is in fluid communication with said needle hub;
    a solid tip member distal to said distal openings, wherein said solid tip member comprises at least one blade, the at least one blade having at least one beveled face that extends to a cutting edge disposed at an angle of about 5-45° from an axis perpendicular to a longitudinal axis of said cannula, and wherein the vertical length of said cutting edge is about 50-95% of the diameter of said cannula portion; and
    at least one planar lateral facet spanning an exterior distal region of said cannula portion and an exterior proximal region of said solid tip member, and the at least one lateral facet includes a medial groove running distally from at least one of the distal openings and terminates proximal to said at least one blade.

13. The vial access cannula of claim 12, wherein the at least one blade includes opposing beveled faces that extend to the cutting edge.

14. The vial access cannula of claim 12, wherein the solid tip member includes at least two beveled faces that extend to at least two cutting edges.

15. The vial access cannula of claim 12, wherein the at least one planar lateral facet comprises a pair of planar lateral facets, wherein said pair of planar lateral facets comprises a medial groove, and wherein said medial groove
    (i) is disposed parallel to the longitudinal axis of said cannula,
    (ii) has substantially the same width as said distal openings, and (iii) runs distally from said distal openings and terminates proximal to said at least one blade.

16. The vial access cannula of claim 12, wherein said cutting edge includes two beveled faces disposed at an angle of about 20-40° from the longitudinal axis of said cannula.

17. The vial access cannula of claim 12, wherein said vial access cannula is molded from plastic.

18. A molded plastic vial access cannula comprising:
(i) a needle hub suitable for receiving a hypodermic syringe or an IV set, wherein said needle hub comprises the female portion of a Luer lock;
(ii) a cannula portion connected to the needle hub and having a centrally disposed lumen, wherein said centrally disposed lumen terminates in two laterally disposed distal openings and is in fluid communication with said needle hub;
(iii) a solid tip member distal to said distal openings, wherein said solid tip member comprises
  (a) two bevels, wherein each of said bevels is medially disposed at an angle of about 5-25° from a longitudinal axis of the cannula, and
  (b) at least one blade, the at least one blade having at least one beveled face that extends to a cutting edge disposed at an angle of about 5-45° from an axis perpendicular to a longitudinal axis of said cannula, wherein the vertical length of said cutting edge is about 50-95% of the diameter of said cannula portion, and said cutting edge forming an angle of about 60°; and
(iv) two laterally disposed planar facets, wherein said facets span an exterior distal region of said cannula portion and a proximal region of said solid tip member, wherein at least one of the laterally disposed planar facets includes a medial groove running into the proximal region of the solid tip member, the medial groove substantially spaced from two opposing longitudinal edges of the at least one planar lateral facet.

19. The vial access cannula of claim 18, wherein said at least one blade includes opposing beveled faces that extend to the cutting edge.

20. The vial access cannula of claim 18, wherein the solid tip member includes at least two beveled faces that extends to at least two cutting edges.

21. The vial access cannula of claim 18, wherein each of said two laterally disposed planar facets comprises a medial groove, and wherein each medial groove
(i) is disposed parallel to the longitudinal axis of said cannula,
(ii) has substantially the same width as said distal openings, and
(iii) runs distally from said distal openings and terminates proximal to said at least one blade.

22. The vial access cannula of claim 1, wherein the medial groove extends distally beyond a distal wall portion of the centrally disposed lumen.

* * * * *